US00PP12145P2

(12) United States Plant Patent
Bracken

(10) Patent No.: US PP12,145 P2
(45) Date of Patent: Oct. 16, 2001

(54) OAK TREE NAMED 'PALMETTO PIN OAK'

(75) Inventor: Ray Bracken, Piedmont, SC (US)

(73) Assignee: Ray Bracken Nursery, Inc., Piedmont, SC (US)

( * ) Notice: Subject to any disclaimer, the term of this patent is extended or adjusted under 35 U.S.C. 154(b) by 0 days.

(21) Appl. No.: 09/427,730

(22) Filed: Oct. 27, 1999

(51) Int. Cl.[7] ..... A01H 5/00
(52) U.S. Cl. ..... Plt./225

(58) Field of Search ..... Plt./225

*Primary Examiner*—Bruce R. Campell
*Assistant Examiner*—June Hwu
(74) *Attorney, Agent, or Firm*—C. A. Whealy

(57) ABSTRACT

A new and distinct cultivar of Oak tree named 'Palmetto Pin Oak', characterized by its rapid growth rate; easy to root cuttings; straight trunk; pyramidal plant shape; very freely branching, dense and bushy habit; lateral branches that are angled horizontally or upwardly allowing for easier movement under the trees; small, but numerous leaves; and attractive fall color.

4 Drawing Sheets

BACKGROUND OF THE INVENTION

The present invention relates to a new and distinct cultivar of Oak tree, botanically known as *Quercus palustris×phellos,* and hereinafter referred to by the name 'Palmetto Pin Oak'.

the new Oak tree is a product of a planned breeding program conducted by the Inventor in Piedmont, S.C. The objective of the breeding program is to create new fast-growing Oak tree cultivars that are freely branching with horizontal to upwardly angled branches, densely foliage, easily propagated, and have a desirable plant form.

The new cultivar originated from a cross made by the Inventor of an unidentified selection of *Quercus palustris,* or Pin Oak, as the female, or seed, parent with an unidentified selection of *Quercus phellos,* or Willow Oak, as the male, or pollen, parent.

The cultivar Palmetto Pin Oak was discovered and selected by the Inventor as a single seedling within a large progeny population of the stated cross in a controlled environment in Piedmont, S.C.

Asexual reproduction of the new Oak tree by stem cuttings since 1989 harvested in a controlled environment in Piedmont, S.C., has shown that the unique features of this new Oak tree are stable and reproduced true to type in successive generations.

BRIEF SUMMARY OF THE INVENTION

The new Oak tree has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Palmetto Pin Oak'. These characteristics in combination distinguish 'Palmetto Pin Oak' as a new and distinct cultivar:

1. Rapid growth rate.
2. Easy to root cuttings.
3. Straight trunk.
4. Pyramidal plant shape.

5. Very freely branching, plants are dense and bushy.
6. Lateral branches horizontal or upwardly angled allowing for easier movement under the trees.
7. Small, but numerous leaves; densely foliated.
8. Attractive fall color.

Plants of the new Oak tree can be compared to plants of the female parent, the unidentified selection of *Q. palustris*. However, in side-by-side comparisons conducted in Piedmont, S.C., plants of the new Oak tree differ from plants of the unidentified selection of *Q. palustris* in the following characteristics:

1. Plants of the new Oak tree are faster growing than plants of the unidentified selection of *Q. palustris.*
2. Plants of the new Oak tree are more freely branching and denser than plants of the unidentified selection of *Q. palustris.*
3. Lateral branches of plants of the new Oak tree are more upwardly orientated than lateral branches plants of the unidentified selection of *Q. palustris* which tend to be drooping.
4. Plants of the new Oak tree have smaller leaves than plants of the unidentified selection of *Q. palustris.*
5. Cuttings of plants of the new Oak tree are easier to root than cuttings of plants of the unidentified selection of *Q. palustris.*

Plants of the new Oak tree can be compared to plants of the male parent, the unidentified selection of *Q. phellos*. However, in side-by-side comparisons conducted in Piedmont, S.C., plants of the new Oak tree differ from plants of the unidentified selection of *Q. phellos in the following characteristics:*

1. Plants of the new Oak tree are faster growing than plants of the unidentified selection of *Q. phellos.*
2. Plants of the new Oak tree are more freely branching and denser than plants of the unidentified selection of *Q. phellos.*
3. Plants of the new Oak tree have a pyramidal plants shape whereas plants of the unidentified selection of *Q. phellos* have a rounded plant shape.

4. Cuttings of plants of the new Oak tree are easier to root than cuttings of plants of the unidentified selection of *Q. phellos.*

5. Fall leaf color of plants of the new Oak tree is red (similar to *Q. palustris*) whereas fall leaf color of plants of the unidentified selection of *Q. phellos is yellow.*

BRIEF DESCRIPTION OF THE PHOTOGRAPHS

The accompanying colored photographs illustrate the overall appearance of the new Oak tree, showing the colors as true as it is reasonably possible to obtain in colored reproductions of this type.

The photograph on the first sheet comprises a side perspective view of a typical tree of 'Palmetto Pin Oak'.

The photograph on the second sheet comprises a close-up view of a typical tree of 'Palmetto Pin Oak' showing the upward lateral branch angle.

The photograph on the third sheet comprises a close-up view of a typical lateral branch of 'Palmetto Pin Oak' showing the foliage density.

The photograph at the top of the fourth sheet comprises a close-up view of typical leaves of 'Palmetto Pink Oak' showing three typical leaf shapes. The leaf shape in the center is predominant.

The photograph at the bottom of the fourth sheet comprises a close-up view of typical leaves of 'Palmetto Pin Oak' (left), an unidentified selection of *Q. palustris* (center), and *Q. phellos* (right) showing the relative leaf size and shape differences between the three plants.

Foliage colors in the photographs may appear different from the actual colors due to light reflectance.

DETAILED BOTANICAL DESCRIPTION

The aforementioned and following observations, measurements, values, and comparisons describe trees grown in Piedmont, S.C., under outdoor nursery conditions which closely approximate commercial production conditions. Plants used for this description were about seven years old.

In the following description, color references are made to The Royal Horticultural Society Colour Chart except where general terms of ordinary dictionary significance are used.

Botanical classification: *Quercus palustris×phellos* cultivar Palmetto Pin Oak.

Parentage:

*Female, or seed, parent.*—Unidentified selection of *Quercus palustris*, or Pin Oak, not patented.

*Male, or pollen, parent.*—Unidentified selection of *Quercus phellos*, or Willow Oak, not patented.

Propagation:

*Type.*—By stem cuttings.

*Time to root.*—About 3 to 4 months are required to initiate roots.

*Root description.*—Fleshy.

Plant description:

*Plant type.*—Deciduous tree.

*Growth habit.*—Upright; pyramidal with rounded crown; dense and full.

*Crop time.*—About seven years from a rooted liner are required to attain a 10-cm trunk caliper.

*Branching habit.*—Very freely branching with about 17 branches per meter. Branches orientated horizontal to upright allowing easier movement under the tree.

*Plant height, soil level to top of leaves.*—Plants will ultimately attain a height of about 25 m.

*Plant diameter, area of spread.*—Plants will ultimately attain a diameter of about 16 m or about ⅔ the height of the tree.

*Growth rate.*—Rapid.

*Bark texture.*—Young: Smooth. Mature: Longitudinally ridged.

*Bark color.*—Young: 197A. Mature: 198A.

*Internode length.*—About 8 mm.

Foliage description:

*Arrangement.*—Alternate.

*Length.*—About 9.2 cm.

*Width.*—About 5.4 cm.

*Shape.*—Broadly ovate.

*Apex.*—Acute to acuminate.

*Base.*—Cuneate.

*Margin.*—Entire to pinnately, deeply lobed. The majority of the leaves, about 95%, are deeply lobed.

*Texture, both surfaces.*—Lustrous; glabrous.

*Venation pattern.*—Pinnate.

*Color.*—Young foliage, upper surface: 144A. Young foliage, lower surface: 146D. Mature foliage, upper surface: 147A, venation, 147A to 147B. Mature foliage, lower surface: 146B, venation, 146B.

*Petiole.*—Length: About 9 mm. Diameter: About 1 mm. Texture: Smooth. Color: 146D.

Flower description:

*Flower appearance/arrangement.*—Flowers monecious; extremely minute. Single female flowers arrange in spikes; male flowers arranged in catkins. Flowers indistinguishable from flowers of plants of selection of *Q. palustris, Q. phellos* and *Q. nigra*. Flowers have no horitcultural nor commercial significance.

*Time to flower.*—Flowering occurs in early April in northern South Carolina.

*Flower buds.*—Shape: Ovoid. Length: about 4 to 5 mm. Diameter: About 2 to 3 mm. Texture: Smooth. Color: Close to 144A.

*Reproductive organs.*—Stamen length: Less than 1 mm. Stamen color: White to pale yellow. Pistil length: Less than 1 mm. Pistil color: White.

*Seed.*—Seed development has not been observed.

Disease pest resistance: Resistance to pathogens or pests common to Oak trees has not been observed.

Hardiness: Plants of the new Oak tree have been observed to be hardy to USDA Hardiness Zone 7.

It is claimed:

1. A new and distinct Oak tree named 'Palmetto Pin Oak', as illustrated and described.

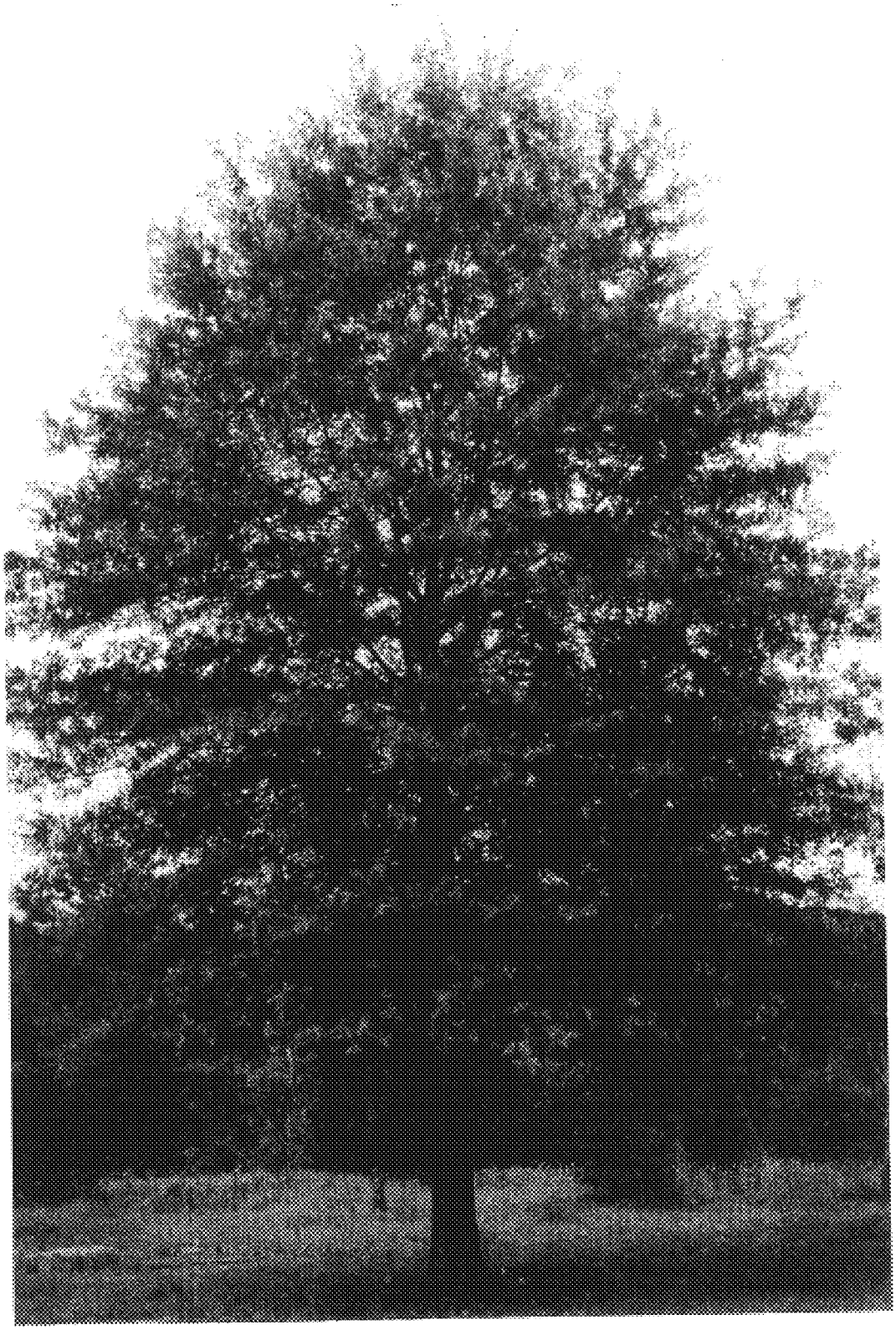

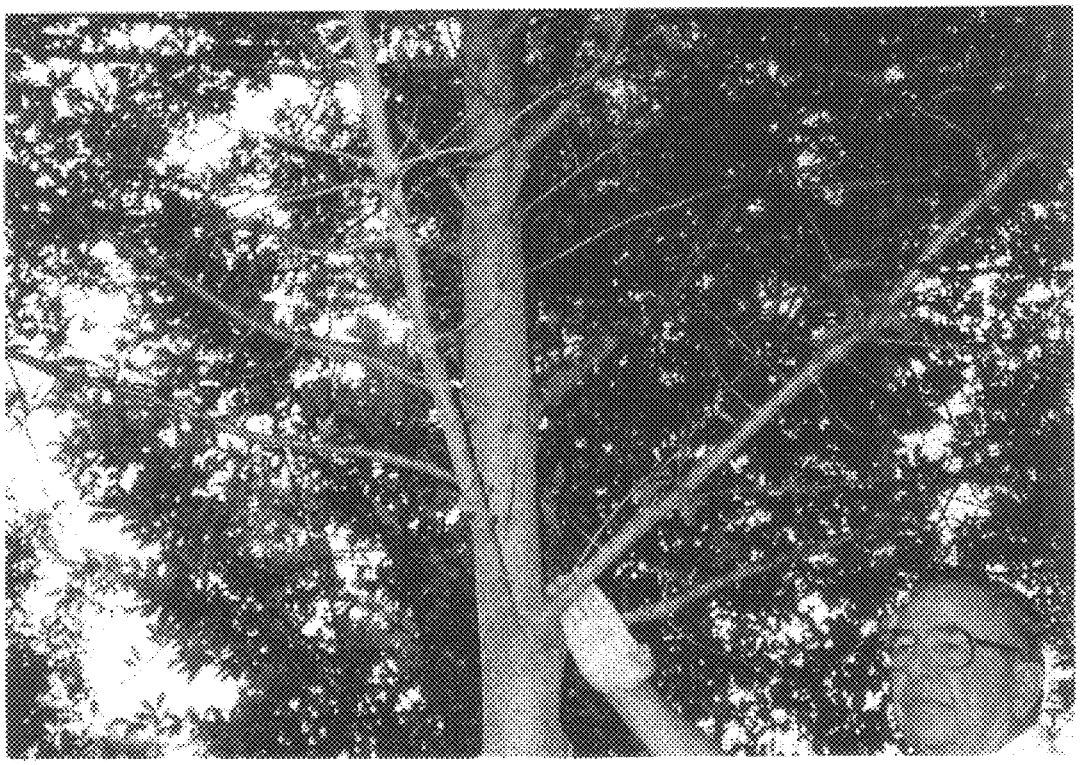

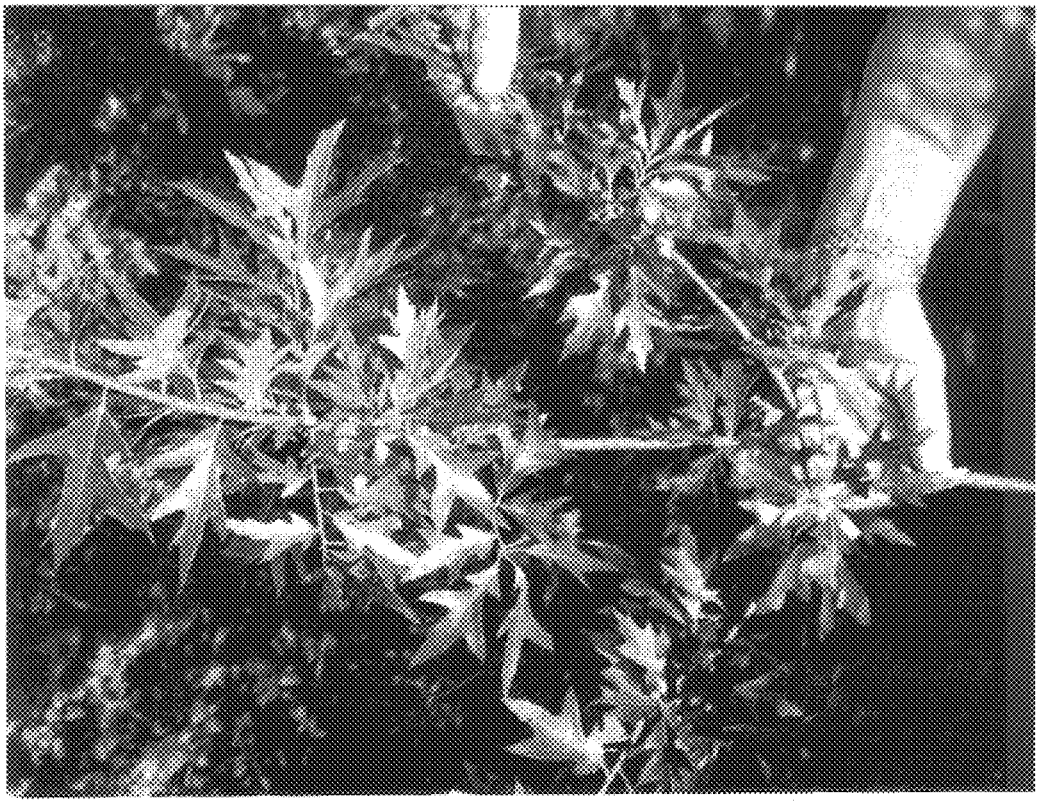

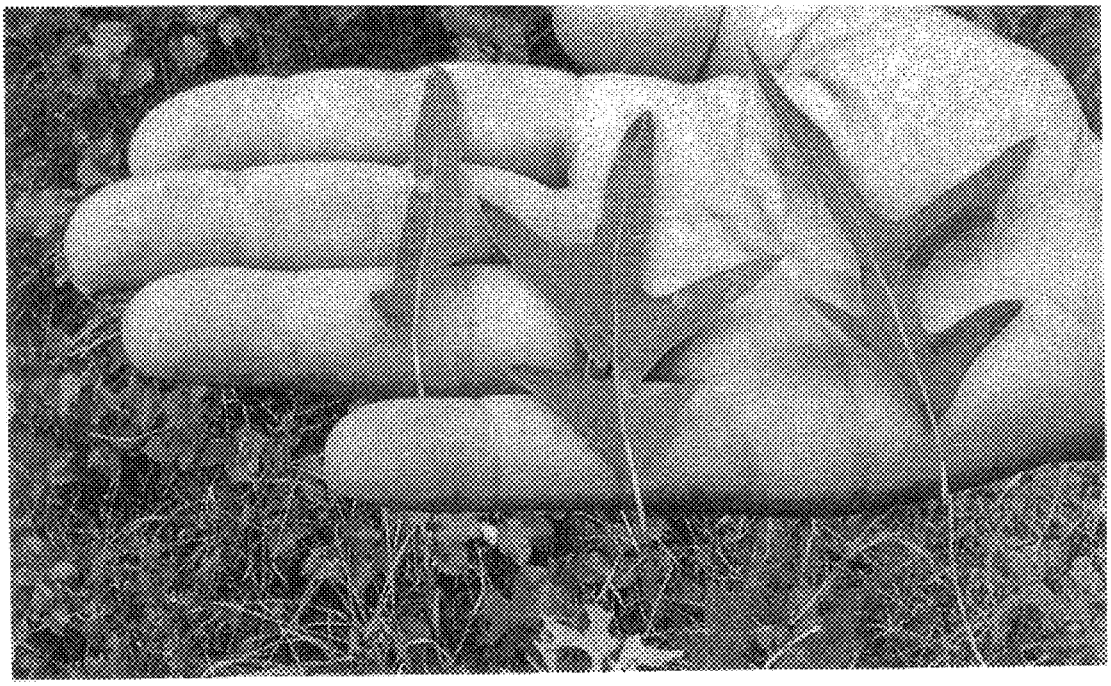
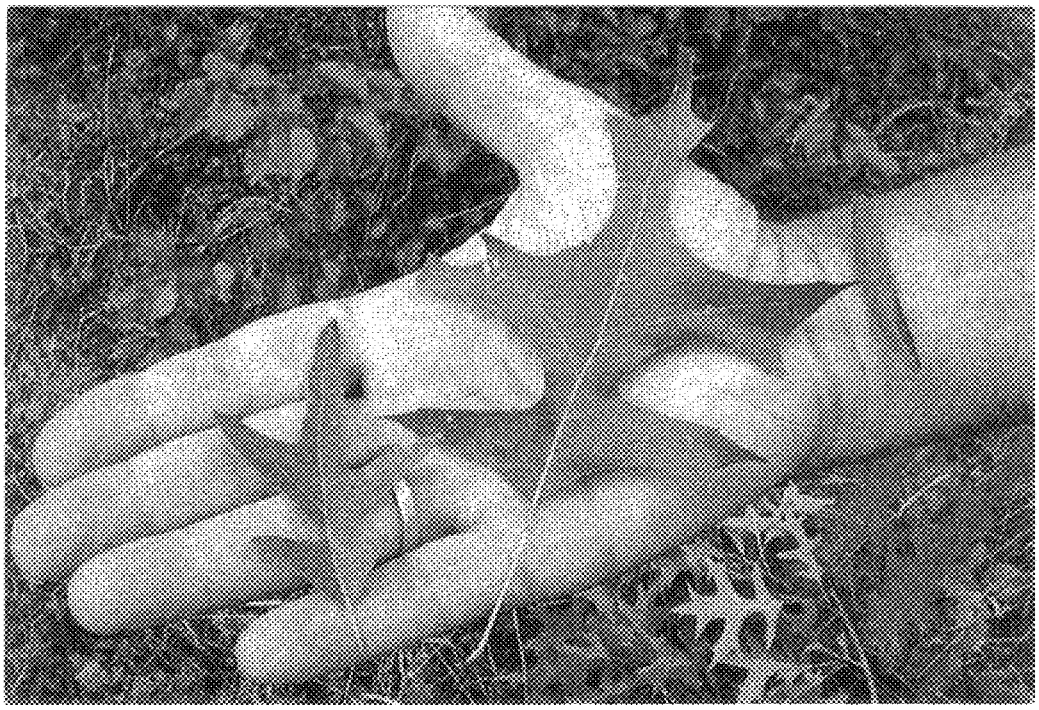

* * * * *